United States Patent [19]

White et al.

[11] 4,449,525
[45] May 22, 1984

[54] PULMONARY RESUSCITATOR

[76] Inventors: Daniel S. White, Rte. 1, Box 25A, Sunrise Beach, Mo. 65079; Jerald L. Nave, P.O. Box 414, Oak Grove, Mo. 64110

[21] Appl. No.: 232,652

[22] Filed: Feb. 8, 1981

[51] Int. Cl.³ .......................................... A61M 16/00
[52] U.S. Cl. ............................................. 128/203.11
[58] Field of Search ..................... 128/202.28, 202.29, 128/203.11, 207.15, 207.12, 205.24, 207.16; 137/DIG. 9, 102

[56] References Cited

U.S. PATENT DOCUMENTS

| | | | |
|---|---|---|---|
| 2,823,670 | 2/1958 | Page | 128/205.24 |
| 3,060,927 | 10/1962 | Gattone | 128/202.28 |
| 3,242,921 | 3/1966 | Seeler | 128/203.11 |
| 3,356,100 | 12/1967 | Seeler | 128/203.11 |
| 3,518,989 | 7/1970 | Seeler | 128/203.11 |
| 3,628,532 | 12/1971 | Magrath | 128/204.25 |
| 3,874,377 | 4/1975 | Davidson | 128/207.15 |
| 4,106,502 | 8/1978 | Wilson | 128/203.11 |

FOREIGN PATENT DOCUMENTS 57022  3/1969  Poland .............................. 128/203.11

Primary Examiner—Henry J. Recla
Attorney, Agent, or Firm—Litman, Day & McMahon

[57] ABSTRACT

A pulmonary resuscitating device designed for single time use and for use with administering cardiopulmonary resuscitation to a heart failure patient. The device includes an endotracheal tube for insertion in the patient's trachea, a mouthpiece for a rescuer, and an air passageway therebetween. Included in the air passageway is a two-way valve which allows exhaled air from a rescuer to pass to the patient's lungs while diverting the patient's exhaled air to the atmosphere. An oxygen tap is provided between the rescuer's mouthpiece and the valve to allow oxygen enriched air to be administered to the patient.

12 Claims, 8 Drawing Figures

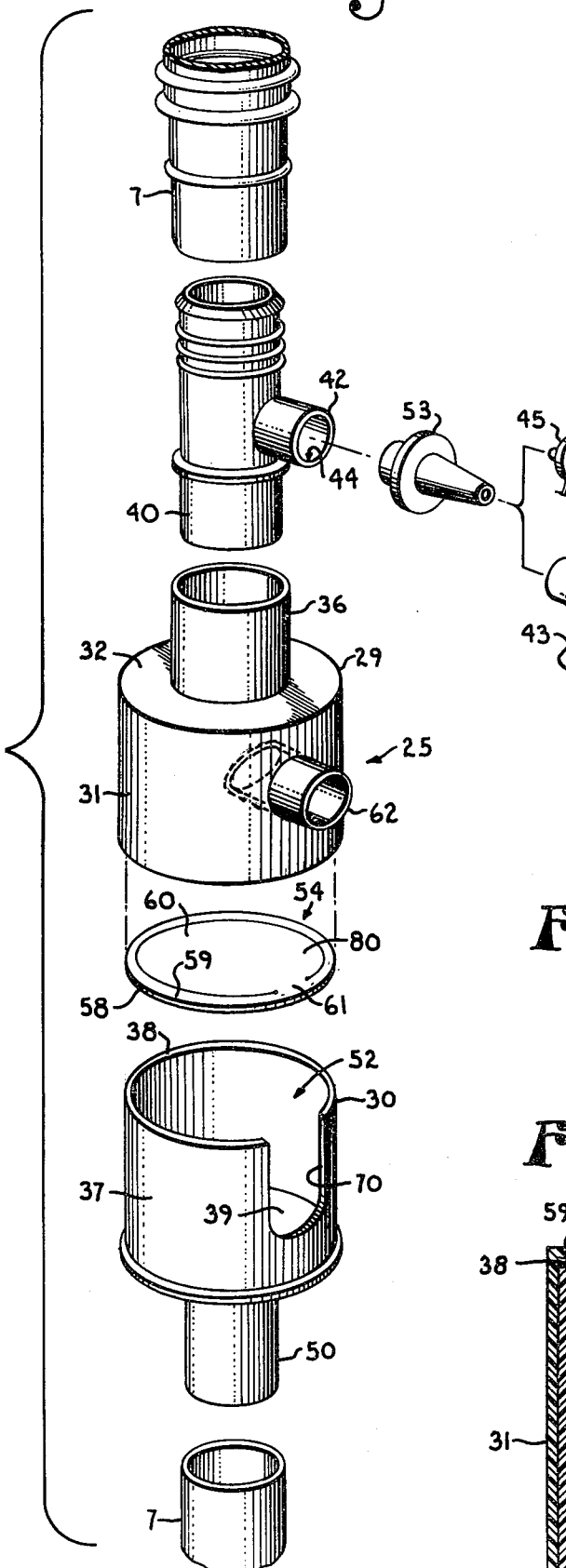
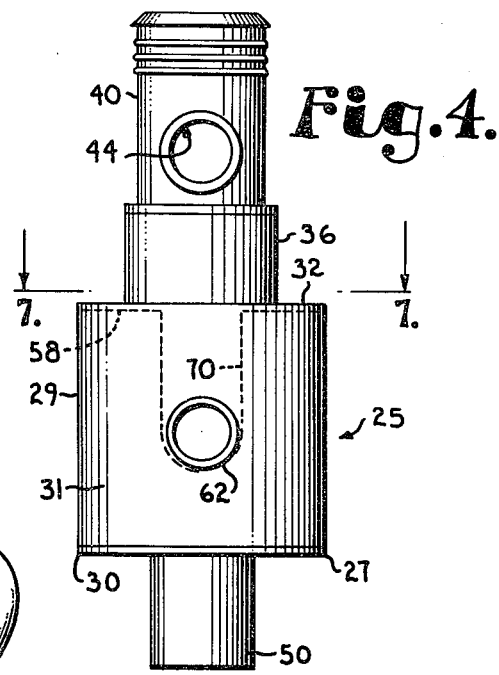
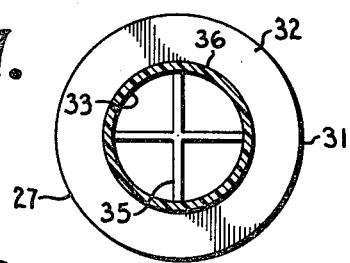
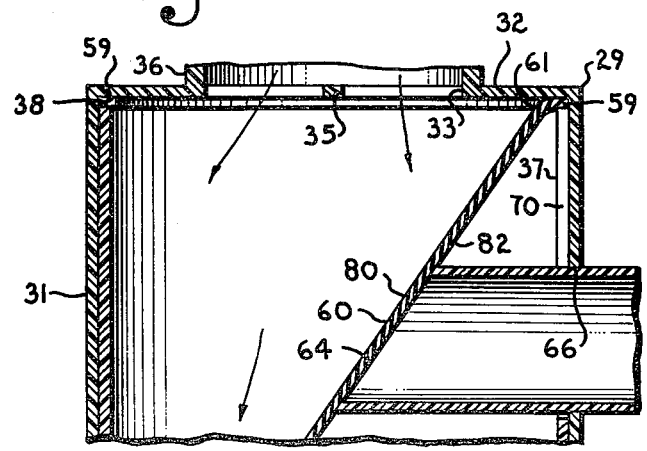

PULMONARY RESUSCITATOR

BACKGROUND OF THE INVENTION

This invention relates to resuscitating devices and in particular to resuscitating devices for use when administering cardiopulmonary resuscitation to a heart failure patient.

Administering cardiopulmonary resuscitation includes performing a cardiac massage while performing mouth-to-mouth resuscitation or the equivalent. Such resuscitation is an excellent means of reviving people whose life processes have failed for various reasons, such as heart attack, electrical shock, or the like. In administering the cardiac massage, it is necessary that a rescuer significantly compress the sternum of the patient in a continual and repetitive fashion. Because of the force required to effectively compress the sternum, the rescuer must kneel alongside the patient's torso and apply downward pressure to the sternum with both arms. Because of this, it is quite difficult for a single rescuer to administer the mouth-to-mouth resuscitation that is helpful in these situations while administering the cardiac massage.

Devices have been designed to allow the sole rescuer to provide the equivalent of mouth-to-mouth resuscitation to a patient while administering the external cardiac massage. These devices typically include air passage means having a mouthpiece at one end for the rescuer and a mouth piece or mask at the other end for the patient.

Drawbacks have existed in the prior art, with one being that existing devices are cumbersome and require a certain amount of time to assemble. Also, existing devices typically have numerous moving mechanical parts which are subject to failure. Further, such conventional devices have normally been relatively expensive and therefore designed to be used numerous times, which necessitates the ability to sterilize the equipment. Because of this, certain medical or paramedical services, such as ambulances, have been unable to use these devices because of their lack of appropriate or suitable sterilizing equipment.

Prior devices have used face masks or the like which must be retained over the mouth of a victim. These devices necessitate the use of straps to secure the mouthpiece to the victim's head before the mask is operable. When using such a face mask, the victim's jaw must be urged outwardly into the breathing position necessitating the movement of the patient's neck which might be quite harmful to accident victims.

Further, prior devices have not included means to provide oxygen enriched air to the patient or means to provide a sufficient volume of air to patients who have lungs which are partially inoperable. This is a problem since some patients who suffer from such infirmities as lung cancer, emphezema, tuberculosis or the like will typically have portions of their lungs damaged to such an extent they will be incapable of passing oxygen to the blood stream yet will be exposed to the air inhaled by the patient. As such, the damaged portions of the lungs will prevent the undamaged portions from being exposed to the air.

OBJECTS OF THE INVENTION

Therefore, the objects of the present invention are: to provide a pulmonary resuscitating device for use by a single rescuer while administering an external cardiac massage to a patient; to provide such a device which includes air passage means having a mouthpiece for the rescuer at one end and an endotracheal tube or other airway for the patient at the other end; to provide such a passageway which includes therein a single two-way valve which allows the air exhaled by the rescuer into the passageway to pass to the patient's lungs but which further prevents the air exhaled from the patient to pass to the rescuer; to provide such a valve which includes a single flappable butterfly which alternately abuts against a grid positioned in the passageway when the rescuer inhales or an exhaust port when the rescuer exhales; to further provide such a passageway which includes at a position between the rescuer's mouthpiece and the valve assembly an oxygen tap, so as to provide oxygen enriched air for the patient; to further provide such a device which is designed for only one-time use; to further provide such a device which is capable of supplying a sufficient volume of air to a patient who has lungs which are partially inoperable; and to provide such a device which is simple in design, easy to manufacture, and particularly well adapted for the proposed usage thereof.

Other objects and advantages of this invention will become apparent from the following description taken in connection with the accompanying drawings wherein are set forth, by way of illustration and example, certain embodiments of this invention.

A pulmonary resuscitating device is provided for use when administering external cardiac pulmonary resuscitation to a patient with heart failure. The device is preferably used one time only and then thrown away. The device includes an air passageway having a mouthpiece for a rescuer at one end and an endotracheal tube or breathing mask at the other end. The endotracheal tube is of common design, having an inflatable cuff at the distal end thereof to prohibit the tube from retracting from the trachea. The passageway includes therein a valve assembly which is designed to allow air as exhaled from the rescuer to flow to the patient's lungs, yet prohibit air exhaled from the patient to flow to the rescuer. Preferably, the valve is a simple one-piece construction. In particular, the disclosed valve includes a two-way flappable vane or disc, an exhaust port, and a grid which is positioned within the passageway and transverse thereto. The flappable disc is activated by air pressure through either exhalation by the rescuer or the patient. When the rescuer exhales, the flappable disc is urged into covering relation with the exhaust port, thereby allowing all of the air exhaled by the rescuer to flow to the patient's lungs. Upon exhalation by the patient, the flappable disc is urged against the transverse grid to sealingly obstruct flow to the rescuer while opening the exhaust port. The flappable disc has an integral hinge which attaches it to an outer portion, which outer portion is firmly secured to the grid so that when the patient exhales, the flappable disc sealingly contacts the outer portion. An oxygen tap is provided at a position between the valve assembly and the rescuer's mouthpiece, allowing oxygen enriched air to be supplied to the patient. The device is generally molded of light-weight plastic and preassembled so that no time is lost in assembling the device prior to administering the cardiopulmonary resuscitation. After the device has been used once, because of its low cost, it is thrown away, thereby allowing such a device to be used by advance medical facilities, such as ambulances, without the need of such facilities acquiring expensive sterilizing equipment.

The drawings constitute a part of this specification and include exemplary embodiments of the present invention and illustrate various objects and features thereof.

BRIEF DESCRIPTION OF THE DRAWINGS

FIG. 3 is an enlarged fragmentary cross-sectional view of the valve body showing the valve flap in the other operable position.

FIG. 4 is an enlarged plan view of the valve body with an oxygen fitting attached.

FIG. 7 is a cross-sectional view of the valve body taken along line 7—7 in FIG. 4.

FIG. 8 is an exploded view of the valve body showing the associated parts thereof.

DETAILED DESCRIPTION OF THE PREFERRED EMBODIMENT

As required, detailed embodiments of the present invention are disclosed herein; however, it is to be understood that the disclosed embodiments are merely exemplary of the invention which may be embodied in various forms. Therefore, specific structural and functional details disclosed herein are not to be interpreted as limiting, but merely as a basis for the claims and as a representative basis for teaching one skilled in the art to variously employ the present invention in virtually any appropriately detailed structure.

Figure 1:
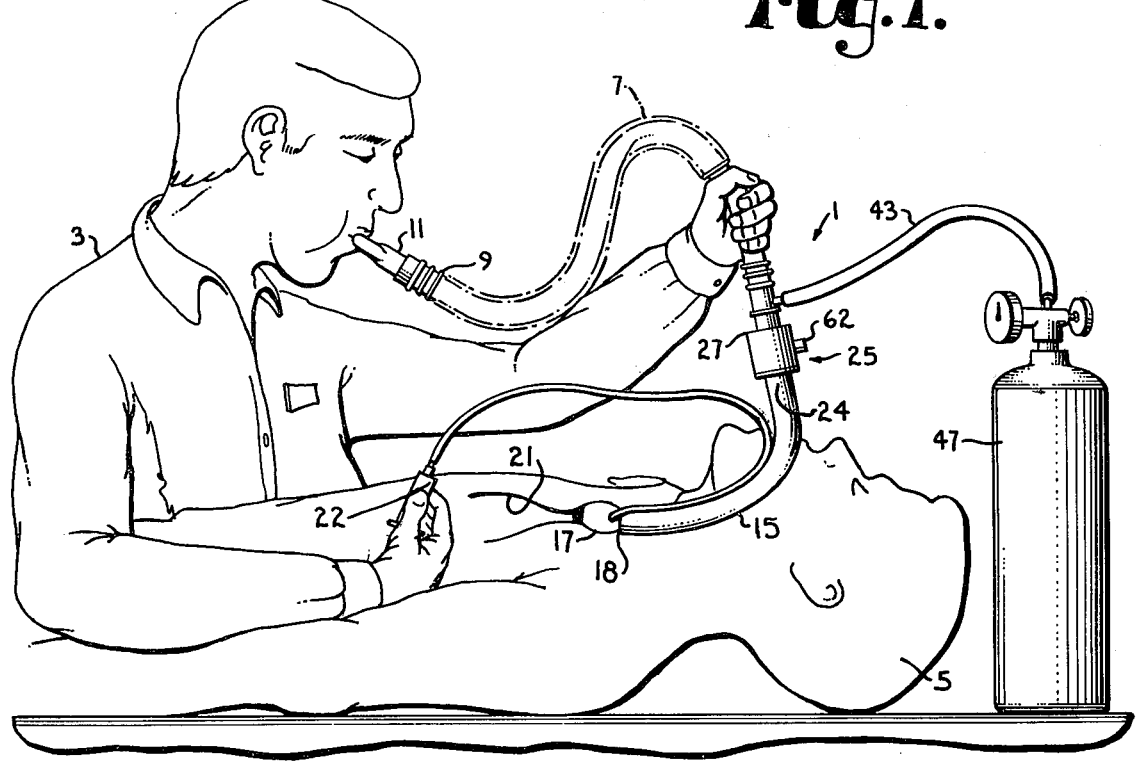
FIG. 1 is a partially schematic view showing a rescuer preparing to administer cardiopulmonary resuscitation to a victim while using a resuscitator according to this invention.

The reference numeral 1 generally designates a pulmonary resuscitator according to the present invention. The resuscitator 1, as is shown in FIG. 1, is being fitted by a rescuer 3 to a patient 5. The rescuer 3 is preparing to simultaneously administer an external cardiac massage to the patient 5 while also performing artificial respiration by means of the resuscitator 1. The resuscitator 1 allows a single rescuer 3 to perform both the external cardiac massage and the artificial respiration without the aid of a second rescuer.

The resuscitator 1 comprises an airway conduit passageway 6 including an air tube 7 suitable for containing an air flow therein and having at a first end 9 thereof a mouthpeice 11 which is adapted to be received in the mouth of the rescuer 3, so that the rescuer 3 may blow therethrough and force air exhaled from the lungs of the rescuer into the tube 7. At a second end of the air tube 7, is a patient air flow means such as an endotracheal tube or other suitable patient ventilation tube 15. It is anticipated that an oralnasal mask (not shown) could also be used as the patient air flow means. As shown in FIG. 1, the endotracheal tube 15 includes an inflatable cuff 17 at a free or distal end 18 thereof which is operably positioned in the throat or air passageway of the patient past the entrance to the patient's esophegus and partially into the patient's trachea 21. After positioning the endotracheal tube 15 in this manner, the inflatable cuff 17 is inflated by operation of the syringe 22 connected therewith, thereby sealing the patient's trachea so that air which is forced through the air tube 7 is forced into the lungs of the patient 5. Further, the seal effectuated by the inflatable cuff 17 prevents foreign substances, such as fluids, to pass from the esophegus to the lungs of the patient 5 during the resuscitation attempt.

Positioned along the resuscitator air tube 7 in an intermediate portion 24 thereof is a valve assembly 25. The valve assembly 25 functions to allow air exhaled from the rescuer 3 to pass through the air tube 7 to the lungs of the patient 5 while prohibiting air exhaled by the patient 5 from passing through the air tube 7 to the rescuer 3. The valve assembly 25 includes a valve body 27 having two slidably interconnecting members, a first member 29 and second member 30, as shown in FIG. 8. The valve body first member 29, has a surrounding side wall portion 31 and end wall portion 32 which includes an inlet aperture or passageway 33 having a stop means such as the illustrated grid 35 transversely positioned therein.

Figure 2:
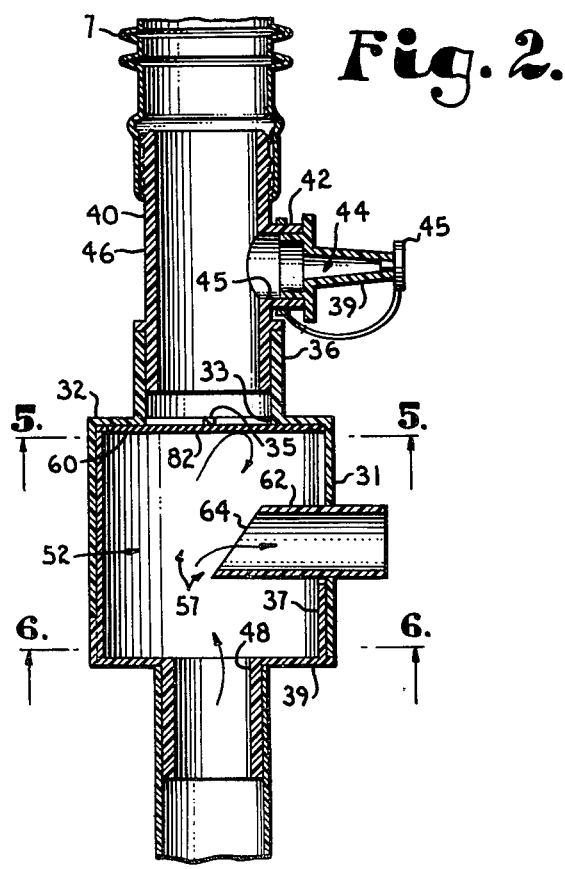
FIG. 2 is an enlarged fragmentary transverse sectional view of a valve body of the invention showing a valve flap in one of two operable positions.
Figure 5:
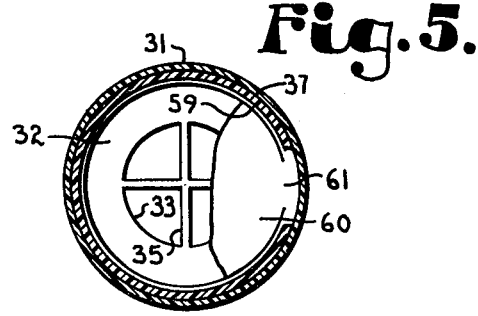
FIG. 5 is a cross-sectional view of the valve body taken along line 5—5 in FIG. 2.
Figure 6:
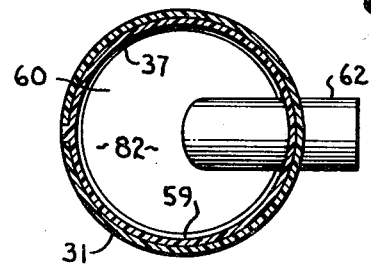
FIG. 6 is a cross-sectional view of the valve body taken along line 6—6 in FIG. 2.

Coaxial with the passageway 33 is a lip or fitting 36 extending outwardly from the first member end portion 32 which allows the valve body first member 27 to be mated directly with an associated portion of the air tube 7, or as shown here, a fitting 40. The fitting 40, as shown in FIG. 2, is slidably received within a portion of the air tube 7. A fluid flow tap 42, including an adapter 53 having a passageway 44 therethrough, flow communicates with an aperture 45 in a wall 46 of the fitting 40 so that a fluid passageway conduit 43 connected to an external fluid supply 47 can be attached to the fitting tap 42. A plug 45 can alternatively be utilized to occlude the opening in the adapter 53 when the conduit 43 is not connected thereto. Preferably, the fluid supply 47 is a cylinder of compressed oxygen with suitable valving and will provide oxygen to the airway tube 7 such that oxygen may be provided to the patient 5 to breath.

The valve body second member 30 includes a side wall portion 37 having an end edge 38, and an end wall portion 39 including an aperture 48 therein. A fitting or lip 50 extends outwardly from the valve body second member end portion 38 and is coaxial with the aperture 48. The second member fitting 50 flow communicates with the patient air flow means. In the present embodiment the fitting 50 is operably mated with a portion of the air tube 7 which extends to the endotracheal tube 15. It is noted that the second member fitting 50 is of a different size than the first member fitting 36 assuring that the valve body 27 can be connected to the associated fittings in a singular orientation thus assuring the resuscitator 1 will function correctly.

The valve body 27 further includes an inner chamber 52 defined by the valve body first member 29 and second member 30, a valve butterfly means 54, an exhaust port 56 and a flap positional means 57. The valve butterfly means 54, as illustrated, comprises a soft pliable member or disk 58 having an outer margin 59 and a center flap portion 60 formed therein with an integral hinge 61 therebetween.

The butterfly disk 58 is made of a suitable thin pliable rubbery material. It is anticipated that the disk 58 could be made of a 1/32-inch thick sheet of neoprene. As shown, the valve body 25 and butterfly means 54 are circular. It is anticipated that the valve body 25 and butterfly means 54 could be of different geometric configuration. The butterfly disk 58 is positioned adjacent the valve body first member passageway 33 such that the disk flap 60 is capable of abuttingly engaging grid 35 to seal the passage 33 from fluid flow therethrough in an upward direction as shown in FIG. 2.

The exhaust port 56 includes a tube 62 having an end 64 which is inserted into the valve body inner chamber 52 through an exhaust port aperture 66 in first member wall portion 31 and slot 70 in second member wall portion 37. The tube end 64 is beveled or angled in a direction toward the valve body first member end portion 32. In particular, the tube end 64 is positioned such that when the flap portion 60 rotates about the hinge 61 so as to engage the tube end 64, the flap portion 60 will substantially seal the tube 62 such that fluid will not exhaust therefrom. It is noted that passageway 33 could extend outwardly into the chamber 52 in which case the end of the passageway 33 would be angled to sealably engage the flap portion 60 in a manner similar to the engagement thereof with the tube 62.

The valve positional means 57 maintains the butterfly flap 60 within an airflow stream passing through the valve body 27 such that directional changes in the airstream rotate the flap 60 from one of the two flap positions to the other, that is from engagement with the passageway 33 or exhaust tube end 64. In the present embodiment the valve positional means 57 includes the passageway grid 35 and the exhaust tube end 64 working in cooperation therebetween. In particular, when the rescuer 3 exhales, the airflow stream in the valve body 27 enters the valve body from the first member passageway 33, as shown by arrows in FIG. 3. This airstream flow impinges on an outer surface 80 of the flap 60 and motivates flap 60 to rotate to a position as shown in FIG. 3. When in this position an inner surface 82 of flap 60 sealingly engages the exhaust tube end 64 yet is presented to potential airstream flow in a direction opposite that shown by arrows in FIG. 3.

After the rescuer 3 exhales, the patient 5 will exhale because of the elasticity of his lungs and heart resuscitation pressure being applied by the rescuer 3. When the patient 5 exhales the airstream flow through the valve body 27 changes to the direction as shown by arrows in FIG. 2. The airstream will not impinge upon the flap inner surface 82 and motivate the flap 60 to rotate to a position against grid 35 and sealing against wall 32, thereby opening the exhaust port 62. The rotation of flap 60 is effectuated by air flow impinging thereon without relying on gravity or the like.

It is noted that the rescuer 3 inhales air around the rescuer mouthpiece 11 or through his nose. In doing so, there is no pressure applied to the flap outer surface 82 which would otherwise act to urge the flap 60 away from grid 35 during exhalation by the patient.

In assembling the valve body 27, the butterfly disk 58 is positioned adjacent and in covering relationship to the first member passageway 33 with the disk outer margin 59 contacting the first member end wall portion 32 and with the flap 60 overlying grid 35. The exhaust port tube 62 is positioned within the aperture 66 in the wall portion 31 of the valve body first member 29. It is noted that the hinge 61 between the butterfly disk and flap is aligned with the exhaust port aperture 66. The valve body second member 30 is slidably mated with the first member 29 such that the exhaust tube 62 is received within the wall portion slot 70. When the valve body second member 30 is slid together with the valve body first member 29, the end shoulder 38 of the second member wall 37 abuts against the outer margin 59 of butterfly disk 58 holding the butterfly disk in place but allowing the flap 60 to rotate on hinge 61. A suitable adhesive is applied to mating surfaces of the valve body 27 to sealingly retain the valve body members 29 and 30 together.

When the valve body 27 is thus assembled, the butterfly flap 60 is capable of rotating between a first position where the flap 60 abuttingly engages the inlet port grid 35 sealing the passageway 33, as in FIG. 2, and a second position where the butterfly flap 60 abuttingly engages the beveled end 64 of the exhaust tube 62 sealing same, as shown in FIG. 3. It is noted that when the flap 60 is in the first position the flap 60 engages and seals the passageway 33 such that the passageway 33 from the inner chamber 52 to the rescuers mouthpiece 11 is sealed from air passing to the mouthpiece 11 from the inner chamber 52. It is also noted that when the butterfly flap 60 is in the second position, as shown in FIG. 3, air passing from the rescuers mouthpiece 11 passes on through the valve body inner chamber 52 and to the patient 5 without passing through the exhaust port 56.

It is noted that the resuscitator 1 is designed to be pre-assembled by the manufacturer and supplied to users in a suitable sterile container (not shown). Further, after use by the user, the resuscitator can be thrown away because of its inexpensive construction.

In use, after positioning the endotracheal tube 15 in the patient 5 as described hereabove, the resuscitator 1 is utilized to allow a single rescuer 3 to provide simultaneously both heart manipulation by pushing on the chest of the patient 5 and ventilation of the patients' lungs through the resuscitator 1.

It is to be understood that while certain embodiments of the present invention have been described and shown herein, it is not to be limited to specific forms or arrangement of parts herein described and shown.

What is claimed and desired to secure by Letters Patent is:

1. A pulmonary resuscitator for use by a single rescuer administering artificial respiration to a patient while simultaneously administering an external cardiac massage to the patient including:
  (a) an elongate air tube means having a first end and a second end and defining an airflow passage therethrough between said ends;
  (b) a mouthpiece attached to said first end of said air tube means adapted to communicate with the mouth of the rescuer;
  (c) patient air flow means attached to said second end of said air tube means, said air flow means providing communication between the lungs of the patient and said air tube means and including securing means to hold said air flow means to said patient so as to free the hands of a rescuer;
  (d) bipositional valve means positioned within said air tube means intermediate said first and second ends and near said second end, said valve means including:
    (1) a valve body having an inner chamber therein, said chamber communicating through said air tube means with said patient air flow means;
    (2) a passageway interconnecting said chamber with said air tube means and said mouthpiece and defining an opening leading into said chamber;
    (3) an exhaust port through said valve body and communicating said chamber with ambient air surrounding said valve body;

(4) a butterfly flap positioned within said valve body and including an outer surface and an inner surface; said flap being alternatively positionable between a first position, wherein said flap outer surface sealably abuts against said passageway opening and blocks air flow from said chamber to said passageway such that air exhaled from said patient is directed through said exhaust port and prevented from passing through said valve body passageway to said rescuer, and a second position, wherein said flap inner surface sealably abuts against said exhaust port such that air exhaled by said rescuer passes through said chamber of said air tube means to the lungs of said patient and is prevented from exiting said exhaust port;

(5) hinge means connecting said flap to said valve body and maintaining said flap within the air flow stream passing through said valve body such that reciprocal breathing motivates said flap to rotate between said first and second positions; and (6) positional means for maintaining said flap within the air flow stream passing through said valve body such that a directional change in the air flow stream motivates said flap to rotate from one of said flap positions to the other of said flap position; and (e) a compressed oxygen tap adapted to be connected to a compressed oxygen source and communicating freely and without restriction with said air flow passage of said air tube means to provide continuous flow from said compressed oxygen source to said airflow passage; said tap being located near said valve means and said tube means being valveless between said tap and said mouthpiece so as to allow continuous filling of said tube means through said tap; said air tube means providing a reservoir for said oxygen between said mouthpiece and said tap; and said air tube means providing substantially unrestricted and free flow of said oxygen between said mouthpiece and said tap.

2. A resuscitator as set forth in claim 1 wherein:
(a) said air flow means comprises an endotracheal tube, said endotracheal tube having an inflatable cuff attached at a free end thereof; said free end adapted to be received in a trachea of said patient and past an entrance to an esophagus of said patient whereby upon inflation of said cuff said trachea is sealed from fluid flow around said endotracheal tube.

3. A resuscitator as set forth in claim 1, wherein:
(a) said butterfly flap is integrally hinged to a butterfly disk, said butterfly disk including an outer margin; and
(b) said butterfly flap sealingly engages said butterfly disk outer margin when said flap is in said flap first position.

4. A resuscitator as set forth in claim 3 wherein:
(a) said valve body includes a first end wall portion, a second end wall portion, and surrounding side wall portions;
(b) said first end wall portion contains said passageway; and
(c) said butterfly disk outer margin is positioned adjacent said first end wall portion.

5. A resuscitator as set forth in claim 1 wherein:

(a) said passageway includes a stop means positioned therein to prevent said flap to rotate to a position within said air tube.

6. A resuscitator as set forth in claim 1 wherein:
(a) said stop means is a grid.

7. A resuscitator as set forth in claim 6 wherein:
(a) said first end wall includes said opening therein, said opening communicating with said passageway; and
(b) said grid is positioned in said opening.

8. A resuscitator as set forth in claim 7 wherein:
(a) said exhaust port includes an exhaust tube having an end thereof extending into the chamber of said valve body and into pathway of said airflow stream.

9. A resuscitator as set forth in claim 8 wherein:
(a) said exhaust tube end is beveled in a direction toward said first end wall portion.

10. A resuscitator as set forth in claim 9 wherein:
(a) said positional means includes:
(1) said grid, and
(2) said exhaust tube beveled end.

11. An improved pulmonary resuscitator, for use in providing flow communication between a rescuer and a victim; said resuscitator having an air tube and a valve positioned intermediate ends of said tube; said valve comprising:
(a) a valve body, including:
(1) first and second valve body members, each valve body member having a surrounding side wall portion and an end wall portion; said valve body members being slidably interconnected and defining an inner cavity therein such that said end wall portions are located on generally opposite sides of said cavity, said valve body second member surrounding wall portion having an end edge adjacent said valve body first member end wall portion when said valve body members are interconnected;
(2) a fluid flow passageway through said valve body first member end wall portion communicating with said air tube adapted to allow air to pass from the rescuer to the valve body inner cavity;
(3) an aperture through the second valve body member end wall portion communicating with said air tube and adapted to allow air to flow from said valve body inner cavity to the patient;
(4) an exhaust tube having an end thereof extending through said valve body member side walls to said inner cavity, said exhaust tube communicating with ambient air to allow air to flow from said inner cavity to said ambient air; said exhaust tube end beveled in a direction toward said valve body first member end wall portion;
(b) a grid positioned in said passageway;
(c) a butterfly disk having an outer margin and a center flap portion integrally hinged therewith positioned within said inner cavity; said outer margin being snugly held between said second body end edge and said first member end wall and said flap portion is adapted to alternately seal over said passage and said exhaust tube end; said center flap being continuously presented to said stream flow through said valve body; and
(d) said center flap portion overlying said exhaust tube end such that upon exhalation of air from said rescuer, said rescuer exhaled air is adapted to pass through said valve body to said patient; said center flap overlying said passageway and abuttingly engaging said grid such that upon exhalation by said patient, said patient exhaled air is adapted to pass through said exhaust tube to said ambient air.

12. A pulmonary resuscitator for use by a single rescuer administering artificial respiration to a patient while simultaneously administering an external cardiac massage to the patient including:
   (a) an elongate air tube means having a first end and a second end and defining an airflow passage therethrough between said first and second ends;
   (b) mouthpiece means attached to said first end of said air tube means adapted to communicate with the mouth of the rescuer;
   (c) a patient air flow means attached to said second end of said air tube means; said air flow means providing communication between said lungs of the patient and said air tube means; said patient air flow means including securing means for maintaining said air flow means in position relative to a patient when placed thereon;
   (d) a bipositional valve means positioned within said air tube means near said second end; said valve means consisting of an inlet and first and second outlets allowing flow of air from the rescuer to the patient through said first outlet and allowing exhaustion of air from the patient to air ambient atmosphere through said second outlet;
   (e) a compressed air tap adapted to be connected to a compressed air source and to said elongate air tube means upstream of said valve means inlet; said air tap communicating freely and without restriction with said airflow passage of said air tube means to provide continuous flow from a compressed breathable air source to said airflow passage; said tap being located between said bipositional valve means and said first end of said air tube means and near said bipositional valve means such that all flow from said air tube means and said air tap flows through said valve means inlet; said air tube means being valveless and substantially nonrestricted between said tap and said mouthpiece means such that said air tube means is adapted to have the compressed air continuously flow thereinto from said tap and provides a reservoir into which said tap continually injects air for the patient.

* * * * *

UNITED STATES PATENT AND TRADEMARK OFFICE
CERTIFICATE OF CORRECTION

PATENT NO. : 4,449,525

DATED : May 22, 1984

INVENTOR(S) : Daniel S. White, et al.

It is certified that error appears in the above-identified patent and that said Letters Patent is hereby corrected as shown below:

In the statement of Inventorship delete "Jerald L. Nave, P.O. Box 414, Oak Grove, Missouri 64110", as a co-inventor.

In The Claims:
Delete the following claim:

11. An improved pulmonary resuscitator, for use in providing flow communication between a rescuer and a victim; said resuscitator having an air tube and a valve positioned intermediate ends of said tube; said valve comprising:
  (a)  a valve body, including:
     (1)  first and second valve body members, each valve body member having a surrounding side wall portion and an end wall portion; said valve body members being slidably interconnected and defining an inner cavity therein such that said end wall portions are located on generally opposite sides of said cavity, said valve body second member surrounding wall portion having an end edge adjacent said valve body first member end wall portion when said valve body members are interconnected;
     (2)  a fluid flow passageway through said valve body first member end wall portion communicating with said air tube adapted to allow air to pass from the rescuer to the valve body inner cavity;
     (3)  an aperture through the second valve body member end wall portion communicating with said air tube and adapted to allow air to

UNITED STATES PATENT AND TRADEMARK OFFICE
CERTIFICATE OF CORRECTION

PATENT NO. : 4,449,525                                    Page 2 of 3

DATED : May 22, 1984

INVENTOR(S) : Daniel S. White, et al.

It is certified that error appears in the above-identified patent and that said Letters Patent is hereby corrected as shown below:

flow from said valve body inner cavity to the patient;

(4) an exhaust tube having an end thereof extending through said valve body member side walls to said inner cavity, said exhaust tube communicating with ambient air to allow air to flow from said inner cavity to said ambient air; said exhaust tube end beveled in a direction toward said valve body first member end wall portion;

(b) a grid positioned in said passageway;

(c) a butterfly disk having an outer margin and a center flap portion integrally hinged therewith positioned within said inner cavity; said outer margin being snugly held between said second body end edge and said first member end wall and said flap portion is adapted to alternately seal over said passage and said exhaust tube end; said center flap being continuously presented to said stream flow through said valve body; and (d) said center flap portion overlying said exhaust tube end such that upon exhalation of air from said rescuer, said rescuer exhaled air is adapted to pass through said valve body to said patient; said center flap overlying said passageway and abuttingly engaging said grid such that upon exhalation by said patient, said patient exhaled

UNITED STATES PATENT AND TRADEMARK OFFICE
CERTIFICATE OF CORRECTION

PATENT NO. : 4,449,525
DATED : May 22, 1984
INVENTOR(S) : Daniel S. White et al.

It is certified that error appears in the above-identified patent and that said Letters Patent is hereby corrected as shown below:

air is adapted to pass through said exhaust tube to said ambient air.

Signed and Sealed this

Fourth Day of December 1984

[SEAL]

Attest:

GERALD J. MOSSINGHOFF

*Attesting Officer*     *Commissioner of Patents and Trademarks*